(12) United States Patent
McIntyre et al.

(10) Patent No.: US 9,814,407 B2
(45) Date of Patent: Nov. 14, 2017

(54) CARDIOPULMONARY RESUSCITATION COMPRESSION FORCE INDICATOR

(75) Inventors: Allister R McIntyre, County Down (GB); John McCune Anderson, County Down (GB); Johnny Houston Anderson, County Down (GB); James Allen, County Antrim (GB)

(73) Assignee: HEARTSINE TECHNOLOGIES LIMITED, Belfast (GB)

( * ) Notice: Subject to any disclaimer, the term of this patent is extended or adjusted under 35 U.S.C. 154(b) by 1014 days.

(21) Appl. No.: 12/518,733

(22) PCT Filed: Dec. 14, 2007

(86) PCT No.: PCT/EP2007/011000
§ 371 (c)(1),
(2), (4) Date: Jun. 11, 2009

(87) PCT Pub. No.: WO2008/071439
PCT Pub. Date: Jun. 19, 2008

(65) Prior Publication Data
US 2010/0312153 A1    Dec. 9, 2010

(30) Foreign Application Priority Data
Dec. 14, 2006 (IE) .................................. S2006/0916

(51) Int. Cl.
*A61B 5/08* (2006.01)
*A61B 5/053* (2006.01)
*A61H 31/00* (2006.01)
*A61N 1/39* (2006.01)
*G09B 23/28* (2006.01)
*A61B 5/00* (2006.01)

(52) U.S. Cl.
CPC ........... *A61B 5/053* (2013.01); *A61H 31/005* (2013.01); *A61N 1/3925* (2013.01); *G09B 23/288* (2013.01); *A61B 5/7239* (2013.01); *A61H 2201/5061* (2013.01)

(58) Field of Classification Search
USPC ........................... 600/301, 484; 51/301, 484
See application file for complete search history.

(56) References Cited

U.S. PATENT DOCUMENTS

| | | | |
|---|---|---|---|
| 4,619,265 A | 10/1986 | Morgan et al. | |
| 5,496,257 A * | 3/1996 | Kelly | 601/41 |
| 6,351,671 B1 * | 2/2002 | Myklebust et al. | 607/5 |
| 2004/0162587 A1 | 8/2004 | Hampton et al. | |
| 2006/0217624 A1 * | 9/2006 | Myklebust et al. | 600/512 |
| 2007/0060785 A1 * | 3/2007 | Freeman et al. | 600/16 |
| 2007/0276300 A1 * | 11/2007 | Olson et al. | 601/41 |

* cited by examiner

*Primary Examiner* — Navin Natnithithadha
*Assistant Examiner* — Michael R Bloch

(57) ABSTRACT

A cardiopulmonary resuscitation (CPR) compression force indicator includes circuitry (20, 26, 28, 30) for monitoring a patient's transthoracic impedance while the patient is being given CPR and generating a corresponding impedance signal, circuitry (32, 34, 36) for processing the impedance signal to provide an ongoing measurement of cardiac hemodynamic output, a microprocessor (24) for determining if the measurement falls outside pre-set limits, and indicator(s) (38) for indicating such determination externally to the person giving the CPR.

15 Claims, 1 Drawing Sheet

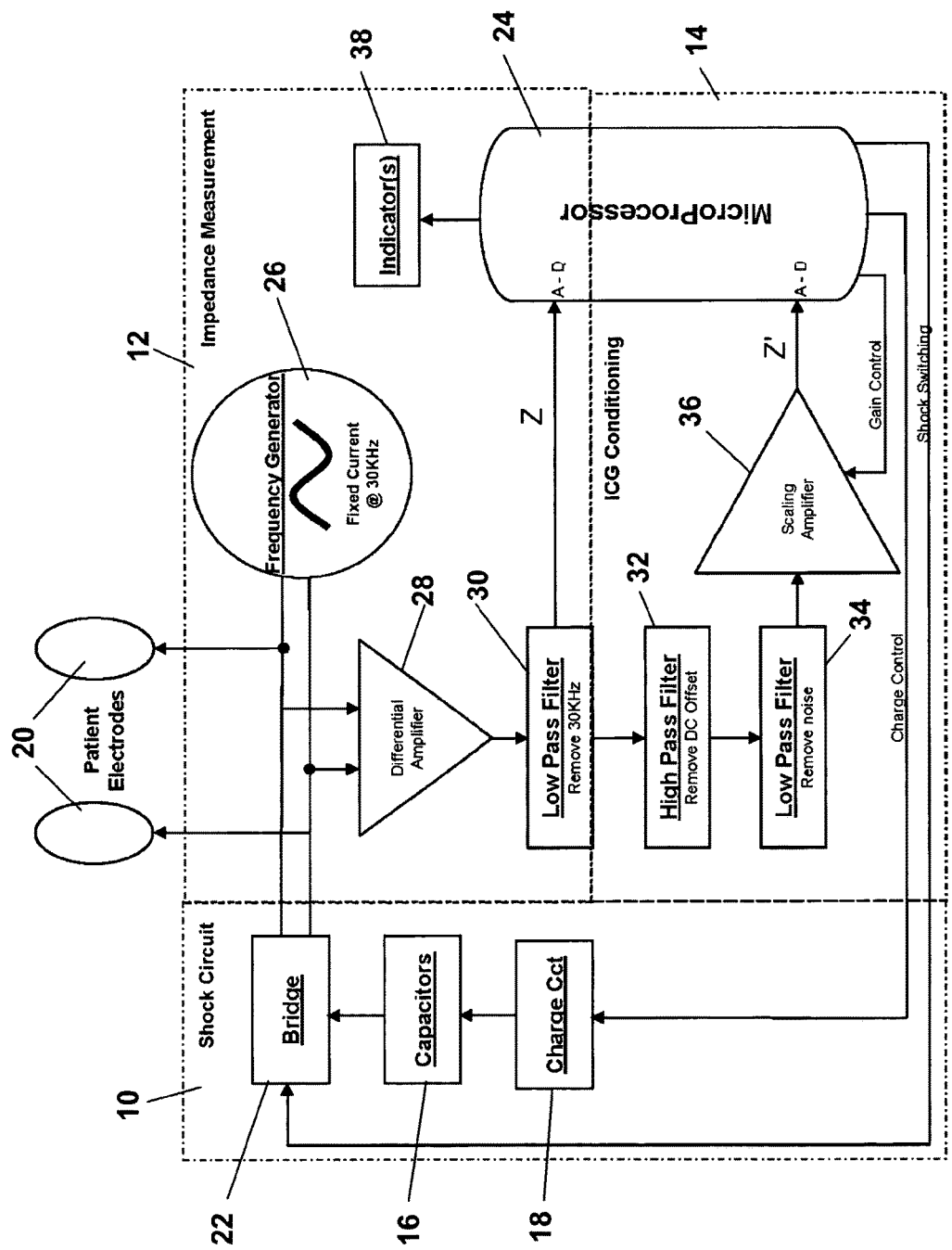

CARDIOPULMONARY RESUSCITATION COMPRESSION FORCE INDICATOR

FIELD OF THE INVENTION

This invention relates to an apparatus and method for indicating the compression force being applied to a patient during cardiopulmonary resuscitation.

BACKGROUND TO THE INVENTION

An impedance cardiogram (ICG) is a measure of cardiac hemodynamic output. Impedance is a measurement of the resistance to the passage of alternating current. Constant, low amplitude, high-frequency current can be passed through the thorax, and the resultant voltage, appearing across the electrodes through which the current is applied to the patient, is a measure of the impedance caused by the blood movement in and out of the heart. Areas of high blood volume present low impedance, and areas of low blood volume resent high impedance. As blood flows and changes in blood volume occur, so the impedance changes and this relationship can be used in the examination of heart function. expiration and inspiration during respiration also causes changes in the thoracic impedance but at a rate much slower than those caused by the heart. By taking the first derivative of the impedance signal, a waveform representing changes in thoracic impedance is produced and, in this form, perturbations and respiratory influences can be more readily filtered out. The result is a waveform (ICG) which represents cardiac hemodynamic output.

In the case of sudden cardiac arrest (SCA), the electrical and hemodynamic functions of the heart all but cease and respiration stops. Under such a condition, electrotherapy should be applied but in conjunction with cardiopulmonary resuscitation (CPR). The rate and force of the application of CPR is critical to a fast and complete recovery of the patient. In terms of rate, if compressions are too slow, the blood will not be circulated quickly enough to sustain the primary organs. If too quick, the heart will not be given sufficient time to fill up with blood prior to its expulsion, by compression, into the aorta. Likewise, insufficient force will not adequately compress the heart causing insufficient blood flow. excessive force may not only damage the ribs and lungs but, in the extreme, damage the heart itself. The current move towards minimal training of those who use defibrillators in emergencies and consumer use in the home exacerbates the need for real-time assistance in CPR technique. It is therefore becoming increasingly important to integrate instruction in CPR with instruction in the use of defibrillators.

PRIOR ART

The prior art teaches the use of a force sensor integrated into electrodes which can be used for monitoring the ECG and transthoracic impedance of a patient and for applying the electrotherapy. When applying CPR, the responder is requested to apply the compressions onto the sensor and can be advised to reduce or increase the force applied according to a comparison between the force applied and that pre-defined in the device. There are a number of problems apparent with this technology.

A first problem is that the two electrodes and the force sensor have to be constructed as a single entity. As a result, the placement of the assembly can be critical and a compromise between the distance between the placement of electrodes and the placement of the force sensor. The choice between anterior-posterior or apex-sternum placement cannot be afforded to the responder. Consequently, paediatric use cannot be offered without an entirely different assembly.

A second problem is that the electrodes are for single-use only and the inclusion of a force sensor is an expensive option not suited to devices which are intended for the consumer or home responder, their primary 'raison d'etre'.

Furthermore, the use of a sensor in an automated compression system is cumbersome in an emergency situation.

SUMMARY OF THE INVENTION

According to the invention there is provided a cardiopulmonary resuscitation (CPR) compression force indicator, comprising means for monitoring a patient's transthoracic impedance while CPR is administered to the patient and generating a corresponding impedance signal, means for processing the impedance signal to provide an ongoing measurement of cardiac hemodynamic output, means for determining if the measurement falls outside pre-set limits, and means for indicating such determination to the person administering the CPR.

The indicator may, but need not, form part of an automated external defibrillator (AED) including patient electrodes for both applying a shock to the patient and obtaining the patient's transthoracic impedance The invention is based on the insight that during CPR the cardiac hemodynamic output is a function of the compression force applied to the patient, and therefore the patient's transthoracic impedance, preferably in the form of the ICG, can provide a reliable measure of that compressive force for feedback to the user, i.e. the person giving the CPR.

In an embodiment of the invention a CPR compression force indicator is incorporated into an AED which advises the user if the force applied during CPR is insufficient, sufficient or excessive. The AED measures the transthoracic impedance of a patient and uses it to increase the specificity of the diagnostic algorithm determining whether or not a shock should be applied. The impedance signal is also processed to obtain the ICG. In the event of CPR following cardiac arrest, the compressive force applied to the chest of the patient during CPR can be measured by the ICG signal response. The user can be advised, by visual and/or voice enunciation, whether the force applied is insufficient, sufficient or excessive.

The invention is capable of implementation in a compact and economical manner and could significantly improve the effectiveness of CPR administration, thereby increasing survival rates post cardiac arrest. This is particularly true in cases of prolonged cardiac arrest when, as the guideline state, CPR should be administered prior to defibrillation.

The invention further provides a method of indicating compression force during cardiopulmonary resuscitation (CPR), comprising monitoring a patient's transthoracic impedance while CPR is administered to the patient and generating a corresponding impedance signal, processing the impedance signal to provide an ongoing measurement of cardiac hemodynamic output, determining if the measurement falls outside pre-set limits, and indicating such determination to the person administering the test.

BRIEF DESCRIPTION OF THE DRAWINGS

The single FIGURE of the drawings is a block diagram of an automated external defibrillator incorporating an embodiment of the invention.

DESCRIPTION OF AN EMBODIMENT OF THE INVENTION

Referring to the drawing, an automated external defibrillator comprises three main sections: 10, 12 and 14.

Section 10 is the main high voltage shock circuitry and comprises a bank of capacitors 16 which are charged up to a high voltage by a charging circuit 18, the charge being released as a bi-phasic high voltage shock through a pair of patient electrodes 20 by a bridge circuit 22. The charging of the capacitors 16 and the shape and duration of the bi-phasic shock waveform is controlled by a microprocessor 24, the actual shock being given by the user pressing a button if the patient's condition is deemed "shockable" as determined by a diagnostic algorithm having the patient's ECG as input. The ECG is derived in known manner, not shown. The process is prompted by voice messages and/or visual prompts output on visual/audio indicators 38 (the indicators are shown in section 12 for diagrammatic simplicity). The audio/visual output indicators 38 may comprise a loudspeaker and/or LED(s).

Section 12 measures the patient's transthoracic impedance using the same electrodes 20 as are used for applying the shock. A generator 26 produces a 30 kilohertz sinusoidal waveform at a constant current of 100 microamperes. This signal is applied across the electrodes 20. When the electrodes are attached to a patient, a voltage across the electrodes is generated which is superimposed on the 30 kHz sinusoid. This voltage is a direct measurement of the transthoracic impedance of the patient. The voltage generated in response to the sinusoid is applied to a differential amplifier 28 which converts it from a differential signal to a single signal referenced to ground potential. The resultant waveform is passed through a low pass filter 30 which removes the original 30 kHz signal leaving a signal Z which is directly proportional to the patient impedance. The impedance signal is used by the microprocessor 24 to set the bi-phasic pulse amplitude and width to ensure that the correct total energy (typically 150 Joules) is delivered to the patient.

The construction and operation of sections 10 and 12 of the AED are well-known in themselves, and it is not thought that further detail is necessary.

Section 14 provides for the further conditioning of the impedance signal Z in preparation for differentiation by the microprocessor 24, and is additional to the existing circuitry for the measurement of patient impedance, section 12. The main purpose of section 14 is to provide a continuous measure of cardiac hemodynamic output during periods of CPR administration following a shock being given by the shock circuit 12 but, as will be described, it can also be used to provide the ICG as input to the diagnostic algorithm during the non-CPR periods.

Immediately following a shock, an in-built metronome (not shown, but conventional in the art) is started at 100 beats a minute as a guide for the person administering cardiopulmonary resuscitation. This continues for a period of 2 minutes, this being the recommended CPR period following a shock and before a subsequent shock should be given.

In section 14 of the defibrillator the impedance signal which is output from the low pass filter 30 is passed through a high pass filter 32 which removes the dc offset before removing higher frequency noise in the low pass filter 34. The signal is now passed through a low pass filter 34 to remove higher frequency noise. Finally the signal is scaled in an amplifier 36 incorporating digital gain control to a level appropriate for analogue-to-digital conversion by the microprocessor 24. The result is an impedance signal Z' which differs from the signal Z in respect of filtering and amplification, but is still a measure of the patient's transthoracic impedance. The signal Z' is digitally converted and then differentiated by software in the microprocessor to derive a (digital) ICG. By examining the ICG during cardiopulmonary resuscitation the microprocessor 24 can determine whether the compressive force being applied during CPR is insufficient, sufficient or excessive. This is done by defining upper and lower thresholds such that, if the peak ICG voltage exceeds the upper threshold the compressive force is deemed excessive. Likewise, if the peak ICG voltage is below the lower threshold the compressive force is deemed inadequate. Only if the peak ICG voltage lies between the upper and lower thresholds is the compressive force deemed to be adequate.

An indication as to whether more, the same or less pressure should be applied during CPR is achieved through the microprocessor-control of voice messages and/or visual indications output on the indicators 38. In the preferred embodiment, a tri-state LED is used such that if less pressure is to be applied, the indicator shows one color, if more is to be applied, the indicator shows a different color and if the pressure is adequate, a third color is displayed. Alternative embodiments are a single LED varying in intensity, three LEDs, one for each condition, symbols/icons appearing on a display screen, or voice messages, or a combination of two or more of these.

The particular upper and lower thresholds chosen may be fixed or may vary according to patient age, build and/or weight. For example, a child will normally require substantially less compression than an adult. These patient variables may be input automatically to the microprocessor 24, or entered manually. The gain of the amplifier 36 can likewise be fixed or may vary according to the same patient variables, it being understood that the ICG amplitude will be substantially greater for adults undergoing strong compression than for a child undergoing light compression. The variations in threshold levels and amplifier gain can be derived empirically from research into the range of compressive forces which are deemed appropriate for a range of individuals. It would also be possible to use the defibrillator for paediatric patients by changing the electrodes 20. This change can be sensed by the defibrillator and therefore could be used to automatically change the compressive force threshold levels applicable to a child.

Although the preceding has described a system in which the CPR period is fixed at 2 minutes, it would be possible to define the duration of the CPR period as a function of the number of "adequate" compressions, i.e. for which the indicators 38 showed adequate levels of compression.

In a modification of the above embodiment, the microprocessor can be programmed to compare the actual rate at which CPR is applied, as derived from the ICG, with the metronome rate, and indicate to the user, by voice messages and/or visual indications output on the indicators 38, if the CPR is being applied at the correct rate, i.e. within a pre-set range centered on the metronome rate, at too slow a rate (below the range) or too fast a rate (above the range).

As mentioned above, the ICG produced by differentiation of the signal Z' derived by section 14 of the defibrillator is preferably used, during periods when CPR is not being administered, as a further input to the diagnostic algorithm in addition to the patient's ECG. This provides a further refinement of the algorithm, for example, if the patient is judged by the algorithm to be in ventricular tachycardia (VT). Some forms of this are shockable, others not. The ICG can be used to determine if, while in VT, there is sufficient blood-flow. If not, the patient can be shocked accordingly. In this case, in order to use the full range of the A-D conversion, the gain of the amplifier 36 will need to be set higher during the non-CPR periods because the amplitude of the ICG will typically be substantially lower during those periods than during periods of administration of CPR.

Although the above embodiment uses the ICG (first derivative of the patient's transthoracic impedance) as a measure of cardiac hemodynamic output, other feature(s) or characteristic(s) of the patient's transthoracic impedance could be used.

Whilst the invention has been embodied in an automated external defibrillator, it is possible that a stand-alone CPR compression force indicator could be made according to the principles of the present invention, i.e. independent of a defibrillator.

The invention is not limited to the embodiments described herein which may be modified or varied without departing from the scope of the invention.

The invention claimed is:

1. A cardiopulmonary resuscitation compression force device, comprising:
   a processor configured to perform operations comprising:
      receiving, via a pair of electrodes configured to be in contact with a patient, a transthoracic impedance measurement of the patient;
      computing a first derivative of the transthoracic impedance measurement, to yield an impedance cardiogram;
      identifying, within the impedance cardiogram, a peak voltage;
      comparing the peak voltage to an upper threshold voltage, to yield a first comparison, wherein when the peak voltage exceeds the upper threshold voltage, the first comparison indicates a compression force is excessive;
      comparing the peak voltage to a lower threshold voltage, to yield a second comparison, wherein when the peak voltage is below the lower threshold voltage, the second comparison indicates the compression force is inadequate;
      determining based on both the first comparison and the second comparison, how much force to apply in subsequent cardiopulmonary resuscitation to yield a determination; and
      outputting, based on the determination, instructions; and
   an indicator, wherein the indicator receives the instructions from the processor and issues a notification to a user, wherein the notification indicates to the user that a force applied in subsequent cardiopulmonary resuscitation should be maintained or adjusted.

2. The cardiopulmonary resuscitation compression force device as of claim 1, wherein the notification comprises at least one of an audible signal or a visual signal.

3. The cardiopulmonary resuscitation compression force device of claim 2, the processor being further configured to perform operations comprising:
   calculating, based on the first derivative of the transthoracic impedance measurement, a rate at which compressions are applied during cardiopulmonary resuscitation;
   comparing the rate to a metronome rate, to yield a speed comparison;
   second determining based on the speed comparison, whether the rate is too fast or too slow; and
   issuing, via the indicator, a second notification as a result of the second determining, wherein the second notification instructs the user that a rate applied in subsequent cardiopulmonary resuscitation should be maintained or adjusted.

4. The cardiopulmonary resuscitation compression force device as of claim 1, the processor being further configured to perform operations comprising:
   calculating, based on the first derivative of the transthoracic impedance measurement, a rate at which compressions are applied during cardiopulmonary resuscitation;
   comparing the rate to a metronome rate, to yield a speed comparison;
   second determining based on the speed comparison, whether the rate is too fast or too slow;
   outputting second instructions as a result of the second determining, wherein the indicator receives the second instructions from the processor and issues a second notification to the user, wherein the second notification instructs the user that a rate applied in subsequent cardiopulmonary recitation should be maintained or adjusted.

5. The cardiopulmonary resuscitation compression force device of claim 1, wherein the upper threshold voltage is based on at least one of weight of the patient and build of the patient.

6. An automated external defibrillator comprising:
   a pair of electrodes;
   a processor configured to perform operations comprising:
      receiving, via the pair of electrodes configured to be in contact with a patient, a transthoracic impedance measurement of the patient;
      computing a first derivative of the transthoracic impedance measurement, to yield an impedance cardiogram;
      identifying, within the impedance cardiogram, a peak voltage;
      comparing the peak voltage to an upper threshold voltage, to yield a first comparison, wherein when the peak voltage exceeds the upper threshold voltage, the first comparison indicates a compression force is excessive;
      comparing the peak voltage to a lower threshold voltage, to yield a second comparison, wherein when the peak voltage is below the lower threshold voltage, the second comparison indicates the compression force is inadequate;
      determining based on both the first comparison and the second comparison how much force to apply in subsequent cardiopulmonary resuscitation to yield a determination; and
      outputting instructions based on the determination; and
   an indicator, wherein the indicator receives the instructions and issues a notification to a user, wherein the notification instructs the user that a force applied in subsequent cardiopulmonary resuscitation should be maintained or adjusted.

7. The automated external defibrillator of claim 6, wherein the notification comprises voice enunciation indicating the force to apply is one of insufficient, sufficient, and excessive.

8. A method comprising:
receiving, via a pair of electrodes configured to be in contact with a patient while cardiopulmonary resuscitation is administered, a transthoracic impedance of the patient;
computing, using a processor coupled with the pair of electrodes, a first derivative of the transthoracic impedance, to yield an impedance cardiogram;
identifying, within the impedance cardiogram, using the processor, a peak voltage;
comparing, using the processor, the peak voltage to an upper threshold voltage, to yield a first comparison, wherein when the peak voltage exceeds the upper threshold voltage, the first comparison indicates a compression force is excessive;
comparing, using the processor, the peak voltage to a lower threshold voltage, to yield a second comparison, wherein when the peak voltage is below the lower threshold voltage, the second comparison indicates the compression force is inadequate;
determining based on both the first comparison and the second comparison, using the processor, how much force to apply in subsequent cardiopulmonary resuscitation; and
issuing instructions as a result of the determining to a user, using an indicator, wherein the instructions indicate to the user that a force applied to subsequent cardiopulmonary resuscitation should be maintained or adjusted.

9. The method of claim 8, further comprising, via the processor:
identifying, based on the first derivative of the transthoracic impedance, a rate at which compressions are applied during the cardiopulmonary resuscitation;
comparing the rate to an upper limit and a lower limit, wherein the upper limit and lower limit are based on a preset range associated with a metronome rate, to yield a speed comparison;
making a second determination based on the speed comparison, whether the rate is too fast or too slow;
using the indicator to issue, as second instructions, a result of the second determination to the user, wherein a rate applied in subsequent cardiopulmonary resuscitation should be maintained or adjusted our indicated to the user per the second instructions.

10. The method of claim 9 further comprising adjusting the rate to be applied in subsequent cardiopulmonary resuscitation in response to the second instructions.

11. The method of claim 8, wherein the instructions comprise at least one of an audible output and a visual output.

12. The method of claim 8, wherein the instructions comprise voice enunciation indicating the force to apply is one of insufficient, sufficient, and excessive.

13. The method of claim 8, further comprising adjusting the force to be applied in subsequent cardiopulmonary resuscitation in response to the instructions.

14. An automated external defibrillator comprising:
a pair of electrodes configured to be in contact with a patient; and
a processor configured to perform operations comprising:
receiving, via the pair of electrodes, a transthoracic impedance measurement of the patient;
computing a first derivative of the transthoracic impedance measurement, to yield an impedance cardiogram;
identifying, within the impedance cardiogram, a peak voltage;
comparing the peak voltage to an upper threshold voltage, to yield a first comparison, wherein when the peak voltage exceeds the upper threshold voltage, the first comparison indicates a compression force is excessive;
comparing the peak voltage to a lower threshold voltage, to yield a second comparison, wherein when the peak voltage is below the lower threshold voltage, the second comparison indicates the compression force is inadequate;
calculating, based on the first derivative of the transthoracic impedance measurement, a rate at which compressions are applied during cardiopulmonary resuscitation;
comparing the rate to a metronome, to yield a speed comparison; and
determining based on the first comparison, the second comparison, and the speed comparison, (a) how much force to apply and (b) any rate change when rate change is necessary, in subsequent cardiopulmonary resuscitation;
issuing, via an indicator, a notification to a user as a result of the determining, wherein the notification instructs the user that a force and a rate applied in subsequent cardiopulmonary resuscitation should be maintained or adjusted.

15. The automated external defibrillator of claim 14, wherein the notification comprises at least one of an audible output and a visual output.

* * * * *